United States Patent [19]

Robinson et al.

[11] Patent Number: 5,135,945
[45] Date of Patent: Aug. 4, 1992

[54] CHOLESTEROL-LOWERING TOCOPHEROL ANALOGS

[75] Inventors: Keith M. Robinson, Glendale; Eric W. Heineke, Cincinnati, both of Ohio

[73] Assignee: Merrell Dow Pharmaceuticals Inc., Cincinnati, Ohio

[21] Appl. No.: 710,647

[22] Filed: Jun. 5, 1991

[51] Int. Cl.$^5$ .................. A61K 31/35; A61K 31/355
[52] U.S. Cl. .................................. 514/456; 514/458
[58] Field of Search .................. 514/458, 459, 456

[56] References Cited

U.S. PATENT DOCUMENTS 4,321,270 3/1982 Sundeen .............................. 424/267
4,603,142 7/1986 Burger et al. ...................... 514/456
4,681,890 7/1987 Kanehira et al. .................. 514/333

FOREIGN PATENT DOCUMENTS 0369874 5/1990 European Pat. Off.

OTHER PUBLICATIONS

CA 83(11):97026n, Cunningham–Mulholland, 1975.

Primary Examiner—Frederick E. Waddell
Assistant Examiner—Kimberly R. Jordan
Attorney, Agent, or Firm—Michael J. Sayles

[57] ABSTRACT

This invention relates to alkylamino alkylene derivatives of certain 2H-1-benzopyrans useful as plasma cholesterol lowering agents and to their end-use application as therapeutic agents.

16 Claims, No Drawings

CHOLESTEROL-LOWERING TOCOPHEROL ANALOGS

This invention relates to alkylamino alkylene derivatives of certain 2H-1-benzopyrans useful as cholesterol lowering agents and to their end-use application as therapeutic agents.

More specifically this invention relates to alkylamino alkylene derivatives of the formula

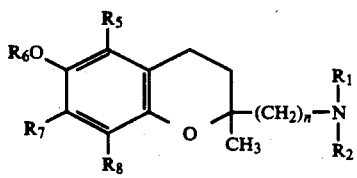

including the (R) and (S) enantiomers and racemic mixtures thereof, and the pharmaceutically acceptable salts thereof, wherein $R_1$ and $R_2$, each individually is a $C_{1-6}$ lower alkyl,
$R_5$ is H or $C_{1-6}$ alkyl,
$R_6$ is H or —C(O)R, R being H or $C_{1-9}$ alkyl,
$R_7$ is H or $C_{1-6}$ alkyl,
$R_8$ is H or $C_{1-6}$ alkyl and n is an integer of 1 to 6.

As used herein, the moiety $(CH_2)_n$ of Formula I wherein n is an integer of one to six represents a $C_{1-6}$ straight or branched-chain alkylene including such preferred species as methylene, ethylene, propylene, t-butylene, n-butylene, n-hexylene and isopropylene. The term "$C_{1-6}$ alkyl" includes the straight and branched-chain radicals having up to six carbon atoms with methyl, ethyl, propyl, n-butyl, t-butyl, pentyl and hexyl being representative. The term "—C(O)R", with R being H or $C_{1-9}$ alkyl, embraces formyl and the straight and branched-chain alkylcarbonyl moieties having up to ten carbon atoms including methylcarbonyl, ethylcarbonyl, propylcarbonyl, t-butylcarbonyl and n-hexylcarbonyl as preferred representatives. When used aryl preferably is phenyl or alkylated phenyl, and aralkyl is benzyl or phenylethyl, and their alkylated derivatives.

In general, the pharmaceutically acceptable salts include those acid addition salts derived by reaction with such acids as hydrochloric, hydrobromic, sulfuric, nitric or phosphoric acids and such organic carboxylic acids as acetic, propionic, glycolic, maleic, tartaric, citric, salicylic, 2-acetyloxybenzoic acids or organic sulfonic acids such as methanesulfonic 4-toluenesulfonic as naphthalenesulfonic acids.

In general the compounds of Formula I may be prepared by standard chemical processes and techniques analogously known in the art. In practice, the preparation of the compounds of Formula I conveniently utilizes 3,4-dihydro-2,5,-7,8-tetramethyl-2H-1-benzopyran-2-ols as starting materials which, for the most part, are known compounds. In those instances wherein any specific starting material is not known then such compounds may readily be prepared using the standard procedures analogously known in the art as well as by applying such processes as would be reasonably expected to produce the desired starting materials.

The preparation of the 3,4-dihydro-2,5,7,8-tetramethyl-2H-1-benxopyran-2-ols and their conversion to the final products of Formula I is depicted in the following reaction scheme.

REACTION SCHEME A:

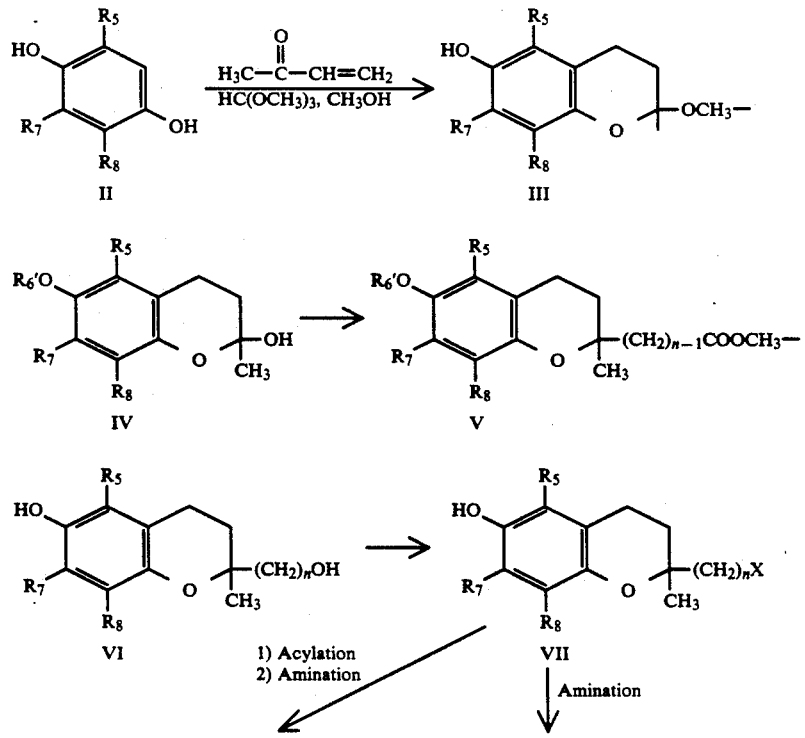

REACTION SCHEME A:
-continued

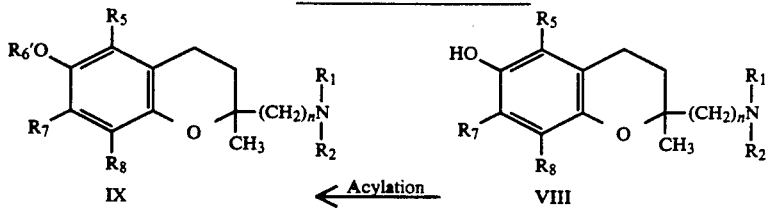

wherein $R_1$, $R_2$, $R_5$, $R_6$, $R_7$, $R_8$ and n are as previously defined, and X is an activating moiety, such as a halide (preferably Cl, Br or I) or $O-S(O)_2R_4$, $R_4$ being H, $C_{1-6}$ alkyl, aryl or aralkyl [preferably a tosylate $CH_2C_6H_5S(O)_2-O$], and $R_6'$ is $-C(O)R$ with R being H or $C_{1-9}$ alkyl.

The reactions of Scheme A entails the condensation of hydroquinones (II) with 3-butene-2-one in the presence of an acid, preferably sulfuric acid, the condensation being effected in methanol and trimethyl orthoformate. The so-produced dihydrobenzopyrans (III) are then sequentially subjected to acylation and hydrolysis reactions according to standard procedures to yield the hemiketals of Formula (IV). Introduction of the hydroxyalkyl moiety at the 2-position of the compounds of Formula (IV) can be effected by Wittig or Horner type reactions, preferably by reaction of the compounds of Formula (IV) with a trimethylphosphonoester (e.g., trimethylphosphonoacetate) to yield the esters of Formula (V) which are hydrolyzed, and then reduced (preferably with lithium aluminum hydride) to yield the alcohols of Formula (VI). These alcohols may also be formed directly by an acid catalyzed condensation of the hydroquinones (II) with the appropriate vinyl diols of Formulae (IX) and (X).

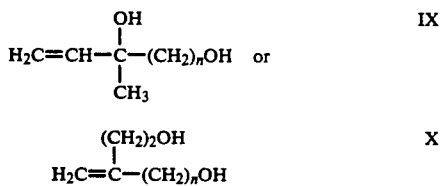

n being as defined above.

Prior to amination, the alcohols of Formula (VI) are first activated by converting the 2-position hydroxyalkyl moieties to either their halides or tosylates (preferably X is a halide or a p-toluenesulfonyl radical) or other equivalently functioning activating moiety, according to standard conditions such as for example reaction of the alcohols with bromotriphenylphosphonium bromide ($\phi_3$PBr$^+$Br$^-$) obtained by reaction of triphenylphosphine with bromine in dichloromethane, or by reacting the alcohols with the appropriate sulfonyl halide (e.g., p-toluenesulfonyl chloride) in the presence of a base according to standard conditions well known in the art. The resulting activated compounds (VII) may be converted to the desired dialkylamino derivatives either before (most preferred) or after acylation of the 6-OH moiety. Standard procedures such as the reaction of the activated moiety with the appropriate dialkylamine, i.e., contacting equimolar quantities of the reactants at temperatures of about 30° C. to 90° C. with stirring in an inert solvent, preferably dimethylformamide, may be used to obtain the dialkylamino derivative, and standard acylation procedures such as reaction of the 6-OH moiety with an acyl halide, acid anhydride or carboxylic acid produce the desired alkylcarbonyloxy moiety at the 6-position.

Further, as there is an asymmetric carbon atom at the 2-position, the compounds may occur as either the R- or the S-enantiomers, or mixtures thereof. The preparation of the individual enantiomeric form may be effected by resolving the acids of Formula (V) by standard and conventional means such as, for example, via the use of diastereomeric salts with optically active amines, or alternatively, by resolving the alcohols (VII) as esters with optically active acids, e.g., L-2,4-MeClC$_6$H$_3$CH-MeCOOH (Me representing methyl).

The following examples will serve to illustrate the techniques and processes described herein.

EXAMPLE 1

3,4-DIHYDRO-2-(2-BROMOETHYL)-2,5,7,8-TETRAMETHYL-2H-1-BENZO-PYRAN-6-OL

To 11.0 g (0.042 mol) of triphenylphosphine in 200 ml of dichloromethane is added dropwise a solution of 6.71 g (0.042 mol) of bromine in 50 ml of dichloromethane. The solution is stirred for 30 min at room temperature, then 10.0 g (0.04 mol) of 3,4-dihydro-6-hydroxy-2,5,7,8-tetramethyl-2H-1-benzopyran-2-ethanol (CAS 79907-48-5) is added. The resulting solution is refluxed for 4 hours, allowed to cool overnight, washed with a solution of 15 g of sodium carbonate in 200 ml of water, dried over anhydrous sodium sulfate, filtered and evaporated. The resulting oil is crystallized from methanol to give 9.22 g of 3,4-dihydro-2-(2-bromoethyl)-2,5,7,8-tetramethyl-2H-1-benzopyran-6-ol.

The optically active enantiomers are obtained by substituting racemic 3,4-dihydro-6-hydroxy-2,5,7,8-tetramethyl-2H-1-benzopyran-3-ethanol with enantiomer R- (CAS 94425-68-0) or S- (CAS-94425-67-9) and by following the procedures of this example for each individual isomer.

EXAMPLE 2

3,4-DIHYDRO-2-(2-BROMOETHYL)-2,5,7,8-TETRAMETHYL-2H-1-BENZO-PYRAN-6-YL ACETATE

To a solution of 9.22 g (0.029 mol) of 3,4-dihydro-2-(2-bromoethyl)-2,5,7,8-tetramethyl-2H-1-benzopyran-6-ol in 60 ml of lutidine is added 30 ml of acetic anhydride. The resulting solution is stirred at room temperature overnight. Water (30 ml) is added and some ice to keep the temperature around 30° C., the mixture is stirred for 30 min, more water and ice are added, the resulting precipitate is collected, washed with water and dried over phosphorus pentoxide under reduced pressure to give 10.0 g of powder. Recrystallization from a mixture of ethyl ether and pentane gives 9.41 g of 3,4-dihydro-2-

(2-bromoethyl)-2,5,7,8-tetramethyl-2H-1-benzopyran-6-yl acetate, m.p. 102°–103° C.

EXAMPLE 3

3,4-DIHYDRO-2-(2-DIMETHYLAMINOETHYL)-2,5,7,8-TETRA-METHYL-2H-1-BENZOPYRAN-6-OL HYDROCHLORIDE

A mixture of 12.53 g of 3,4-dihydro-2-(2-bromoethyl)-2,5,7,8-tetramethyl-2H-1-benzopyran-6-ol and liquid dimethylamine in 50 ml of dimethylformamide is stirred at room temperature for 16 hours. Water is added and the product is extracted with ethyl ether. The extract is washed with water, dried over anhydrous sodium sulfate, filtered and evaporated. One equivalent of hydrochloride acid in isopropanol is added and the resulting precipitate is recrystallized twice from isopropanol/water to yield 9.44 g of the title compound, m.p. >300° C.

EXAMPLE 4

3,4-DIHYDRO-2-(2-DIMETHYLAMINOETHYL)-2,5,7,8-TETRA-METHYL-2H-BENZOPYRAN-6-YL ACETATE HYDROCHLORIDE

A mixture of 3.55 g (0.01 mol) of 3,4-dihydro-2-(2-bromoethyl)-2,5,7,8-tetramethyl-2H-benzopyran-6-yl acetate and 2.0 g of liquid dimethylamine in 50 ml of dimethylformamide is stirred at room temperature for 40 hours. Water is added and the product is extracted with ethyl acetate and ethyl ether. The extract is washed with water, dried over anhydrous sodium sulfate, filtered and evaporated. The resulting oil crystallizes from a mixture of ethyl ether and pentane to give 2.05 g of 3,4-dihydro-2-(2-dimethylaminoethyl)-2,5,7,8-tetramethyl-2H-benzopyran-6-yl acetate as the free base. The hydrochloride salt prepared by standard methods and recrystallized from isopropanol has m.p. 263°–270° C.

EXAMPLE 5

3,4-DIHYDRO-2-(2-DIMETHYLAMINOETHYL)-2,7,8-TRIMETHYL-2H-1-BENZOPYRAN-6-OL

Following the procedure described in Examples 1-3, but using 3,4-dihydro-6-hydroxy-2,7,8-trimethyl-2H-1-benzopyran-2-ethanol (CAS 93600-70-5) as starting material, the title compound is obtained.

EXAMPLE 6

3,4-DIHYDRO-2-(2-DIMETHYLAMINOETHYL)-2,5,8-TRIMETHYL-2H-1-BENZOPYRAN-6-OL

Following the procedure described in Examples 1 and 3, but using 3,4-dihydro-6-hydroxy-2,5,8-trimethyl-2H-1-benzopyran-2-ethanol (CAS 93600-69-2) as starting material, the title compound is obtained.

EXAMPLE 7

3,4-DIHYDRO-2-(2-DIMETHYLAMINOETHYL)-2,5,7-TRIMETHYL-2H-1-BENZOPYRAN-6-OL

Following the procedure described in Examples 1 and 3, but using 3,4-dihydro-6-hydroxy-2,5,7-trimethyl-2H-1-benzopyran-2-ethanol (CAS 93600-68-1) as starting material, the title compound is obtained.

EXAMPLE 8

3,4-DIHYDRO-2(2-DIMETHYLAMINOETHYL)-2,5,7,8-TETRAMETHYL-6-(1,1-DIMETHYL-ETHYLCARBONYLOXY)-2H-1-BENZOPYRAN

Following the procedure described in Example 2, but substituting acetic anhydride by an equimolar amount of pivaloyl chloride, 3,4-dihydro-2-(2-bromoethyl)-2,5,7,8-tetramethyl-2H-1-benzopyran-6-yl α,α-dimethylpropionate is obtained, which is then converted to the title compound by the procedure described in Example 4.

EXAMPLE 9

3,4-DIHYDRO-2-(3-DIMETHYLAMINOPROPYL)-2,5,7,8-TETRA-METHYL-2H-1-BENZOPYRAN-6-OL

Following the procedure described in Examples 1 and 3, but using 3,4-dihydro-6-hydroxy-2,5,7,8-tetramethyl-2H-1-benzopyran-2-propanol (CAS 104568-57-2) as starting material, the title compound is obtained.

Having described the scope of the compounds of this invention as well as the generic and specific methods for preparing said compounds, the following information describes the utility, and the methods therefor, of the compounds of this invention.

Vitamin E, i.e., α-tocopherol, a well known compound of the formula

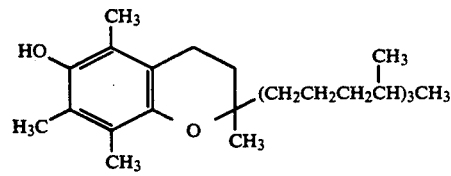

is a natural antioxidant that reacts with oxygen-derived free radicals as well as hydrogen peroxide. It has been shown that it is intercalated in lipid membranes and that its biological function is to protect biomembranes against oxidative attack. The antioxidant 3,4-dihydro-2,5,7,8-tetramethyl-2H-2-benzopyran-6-ol moiety of α-tocopherol is constantly regenerated by the ubiquitous cytosolic redox systems and for all practical purposes is a permanent membrane constituent that is constantly regenerated.

The compounds of this invention also possess a related or similar 3,4-dihydroxy-2,5,7,8-tetraalkyl-2H-1-benzopyran-2-yl moiety, but the 2-position lipophylic moiety of the α-tocopherol molecule, which is thought to be responsible for its ubiquitous incorporation into biomembranes, is replaced with a hydrophylic moiety to impart a greater affinity for cardiac tissue. Thus, the compounds of this invention are also useful as pharmacologic antioxidants and free radical scavengers and, in particular, as scavengers of superoxide anion radical $O_2^-$. They can be therapeutically employed where reperfusion damage due to oxygen-derived free radicals and hydrogen peroxide causes cell death in tissues. This situation arises when total or partial blockade of blood supply to tissues is removed, either spontaneously (transient ischemia) or by pharmacologic or surgical intervention (thrombolysis, angioplasty, by-pass, organ transplant and the like). Tissues subjected to transient ischemia or reperfusion in various disease states, or by their medical treatment, are those of heart, lung, kidney, pancreas and brain. In particular, the now rapidly increasing practice of pharmacologic thrombolysis, also known as reperfusion, after coronary infarct and stroke, will benefit by prior or concomitant administration of a free radical scavenger such as the compounds of this invention. Similarly, surgical interventions, such as percutaneous transluminal coronary angioplasty, where a dilating balloon is used to increase the luminal diameter in severely occluded atherosclerotic vessels, coronary bypass operations, and organ transplant surgery create conditions where reperfusion damage due to oxygen-derived radicals takes place and can be reduced by scavengers. Transient ischemia is one of the causative factors that lead to angina pectoris, and thus the compounds of this invention are also useful as antianginal agents.

The process of inflammation is also known to involve the release of superoxide radicals from phagocytic cells which cause some of the symptoms of rheumatoid arthritis and a free radical scavenger, such as the compounds of this invention, is also useful in the treatment of this disease. The compounds may also be useful in the treatment of cancers, diabetes, and of aging since oxygen-derived free radicals have been identified among causative factors. For reviews, see B. Halliwell and C. Gutteridge, *Biochem. J.*, 219, 1-14 (1984); TINS 1985, 22-6; A.L. Drash, et al., *Am. J. Cardiol.*, 62, 27B-30B (1988).

The subject compounds also exhibit plasma cholesterollowering activity as demonstrated by the following test data.

CD-1 mice from the Charles River Laboratory were fed a diet (Purina Rodent Chow 5001) with or without 3,4-dihydro-2-(2-dimethylaminoethyl)-2,5,7,8-tetramehtyl-2H-1-benzopyran-6-ol for either one or two weeks. Blood samples were collected form the tail vein at 1 week. Two week blood samples were collected from decapitated mice.

In three separate experiments, 3,4-dihydro-2-(2-dimethylaminoethyl)-2,5,7,8-tetramehtyl-2H-1-benzopyran-6-ol consistently lowered plasma cholesterol form 50-80%. The minimum effective dose was an admixture of 0.1% 3,4-dihydro-2-(2-dimethylaminoethyl)-2,5,7,8-tetramehtyl-2H-1-benzopyran-6-ol (Compound A) (i.e., 1 g drug/kg diet) in the diet.

Data are reported as mean ± standard deviation. The "*" indicates values significantly different ($p<0.05$) from control value.

| Treatment | N | Plasma [Chol] (mg/dL) | |
| --- | --- | --- | --- |
| | | at 2 weeks | |
| Control | 10 | 105 ± 20 | |
| 1.0% Compound A | 10 | 29 ± 16* | |
| | | 1 week | 2 weeks |
| Control | 12 | 161 ± 28 | 145 ± 27 |
| 0.1% Compound A | 11 | 75 ± 12* | 67 ± 8* |
| 0.3% Compound A | 11 | 49 ± 16* | 67 ± 8* |
| 1.0% Compound A | 11 | 31 ± 18* | 17 ± 10* |
| Control | 12 | 149 ± 35 | 158 ± 30 |
| 0.01% Compound A | 12 | 136 ± 23 | 143 ± 24 |
| 0.03% Compound A | 12 | 125 ± 23 | 135 ± 27 |
| 0.10% Compound A | 12 | 80 ± 17* | 94 ± 16* |

It can be seen that the treated animals showed a significant drop in plasma cholesterol when compared to the control group in all cases where the administration of Compound A (3,4-dihydro-2-(2-dimethylaminoethyl)-2,5,7,8-tetramehtyl-2H-1-benzopyran-6-ol) was greater than or equal to 0.1%.

CD-1 mice from Charles River were fed a diet (Purina Rodent Chow 5001) with or without Compound A for 1 week. Blood samples were collected from the tail vein at 2, 4, and 7 days on study. Animals were then placed on control diet and tested again after 2 and 4 days (days 9 and 11 on study) after being removed from the drug.

One percent of Compound A lowered plasma cholesterol 74% after 4 days of treatment. The effect was completely reversible 4 days after removal from the drug.

Data are reported as mean ± standard deviation. The "*" indicates values significantly different ($p<0.05$) from control value.

| Treatment | N | Plasma [Chol] (mg/dL) | | | | |
| --- | --- | --- | --- | --- | --- | --- |
| | | day 2 | day 4 | day 7 | day 9 | day 11 |
| Control | 12 | 149 ± 19 | 135 ± 14 | 151 ± 12 | 104 ± 10 | 145 ± 13 |
| 1% of Compound A | 12 | 154 ± 26 | 35 ± 11* | 27 ± 11* | 118 ± 12* | 148 ± 19 |

Db/db mice from Jackson Laboratories were fed a diet (Purina Rodent Chow 5001) with or without Compound A for 40 days (N=12-15/group). The db/db mouse is an animal model of type II diabetes. Blood samples were collected from the tail vein at 10, 20, 30, and 40 days on study.

Compound A lowered plasma cholesterol in a dose-dependent fashion and was effective at the lowest dose used (0.1% of Compound A).

| Treatment | Plasma [Chol] (mg/dL) | | | |
| --- | --- | --- | --- | --- |
| | day 10 | day 20 | day 30 | day 40 |
| Control | 90 ± 11 | 122 ± 36 | 110 ± 27 | 132 ± 11 |
| 0.1% of Compound A | 42 ± 15* | 89 ± 27* | 87 ± 20* | 84 ± 11* |
| 0.3% of Compound A | 19 ± 14* | 43 ± 16* | 45 ± 8* | 52 ± 7* |

Data are reported as mean standard deviation. The "*" indicates values significantly different ($p<0.05$) from control value.

Most preferably, the compounds are administered intravenously particularly under crisis situations wherein it is essential that the therapeutic agent be gotten to its site of action as quickly as possible, such as in those emergency conditions caused by coronary infarction, stroke and surgical interventions, conditions which can cause severe reperfusion damage.

The compounds of this invention can be utilized both prophylactically and therapeutically. The amount of active ingredient for therapeutic administration can vary over a wide range and is dependent upon such factors as the species of mammal to be treated, its age, health, sex, weight, nature and the severity of the condition being treated. Generally, a therapeutically effective amount of the active ingredient to be administered will range from about 0.1 mg/kg to 50 mg/kg of body weight per day. For prophylactic administration, corresponding lower doses can be utilized.

The compounds of this invention also can be orally administered, preferably using more active ingredient per day than when parenterally administered, preferably taking divided doses 3 to 4 times per day. Preferably, enteral administration in post "crisis" situations, particularly after release from hospitalized conditions. The compounds can be used in standard dosage unit forms such as tablets, capsules, dragees, lozenges, elixirs, emulsions, suspensions, and in cases wherein topical application is preferred by suppository or sublingual administration. Tablets and capsules containing from 100 to 400 mg of active ingredient are preferred modes of enteral administration. Of course, in the treatment of inflammation the preferred method of administration is by depot injection directly to the situs of the inflammation area with followup enteral means of administration.

In preparing solid dose forms such as tablets, the active ingredient is generally blended with conventional pharmaceutical carriers or excipients such as gelatin, various starches, lactose, calcium phosphate or powdered sugar. The term pharmaceutical carrier as used herein also includes lubricants employed to improve the flow of tablet granulations and which prevent adhesion of tablet material to the surfaces of tablet dies and punches. Suitable lubricants include, for example, talc stearic acid, calcium stearate, magnesium stearate and zinc stearate. Also included within the definition of a pharmaceutical carrier as used herein, are disintegrating agents added to assist the breakup and dissolution of tablets following administration, as well as coloring and/or flavoring agents to enhance the esthetic qualities of the tablets and make them more acceptable to the patient.

Suitable liquid excipients for the preparation of liquid dosage unit forms include water and alcohols such as ethanol, benzyl alcohol and the polyethylene glycols, either with or without the addition of a surfactant. In general, the preferred liquid excipients, particularly for injectable preparations, include water, physiological and saline solutions, dextrose and glycol solutions such as an aqueous propylene glycol or polyethylene glycol solutions. In order to minimize or eliminate irritation at the site of injection, such compositions may contain a nonionic surfactant having a hydrophile-lipophile balance (HLB) of from about 12 to about 17. The quantity of surfactant in such formulations ranges from about 5 to 15% by weight. The surfactant can be a single component having the above-identified HLB, or a mixture of two or more components having the desired HLB. Illustrative of surfactants useful in parenteral formulations are the class of polyoxyethylene sorbitan fatty acid esters as, for example, sorbitan monooleate and the high molecular weight adducts of ethylene oxide with a hydrophobic base, formed by the condensation of propylene oxide with propylene glycol. In certain topical and parenteral preparations, various oils can be utilized as carriers or excipients. Illustrative of such oils are mineral oils, glyceride oils such as lard oil, cod liver oil, peanut oil, sesame oil, corn oil and soybean oil. For insoluble compounds, suspending agents may be added as well as agents to control the viscosity, as for example, magnesium aluminum silicate or carboxymethylcellulose. In addition to these excipients, buffers, preservatives and emulsifying agents may also be added.

Of course, as is true in most instances wherein certain classes of chemical compounds have been found to have beneficial therapeutic end-use applications, certain subgeneric groups and certain specific compounds are preferred. In this instance the preferred compounds of Formula I are those wherein $R_5$, $R_7$ and $R_8$ are methyl; wherein $R_6$ is formyl, methyl carbonyl, t-butylcarbonyl, ethylcarbonyl, propylcarbonyl, pentylcarbonyl; wherein n is 2 (representing an ethylene moiety), and $R_1$ and $R_2$ substituents attached to the nitrogen atom are methyl. Preferred compounds are those as illustrated in the examples showing the preparation of the compounds of Formula I.

Of course, it is obvious that the 2-position methyl moiety may be removed or replaced with another lower alkyl (e.g., the 2-position methyl may be replaced with H, ethyl, propyl, butyl and the like). Such so-modified compounds are also contemplated within the scope of this invention for the utilities herein alleged, and may be prepared by standard procedures obvious to those skilled in the art.

What is claimed is:

1. A method of lowering plasma cholesterol in a patient in need thereof which comprises administering to the patient an amount of a compound of formula I effective to lower plasma cholesterol

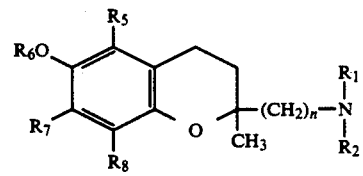

including the (R) and (S) enantiomers and racemic mixtures thereof, and the pharmaceutically acceptable salts thereof, wherein
$R_1$ and $R_2$, each individually is a $C_{1-6}$ lower alkyl,
$R_5$ is H or $C_{1-6}$ alkyl,
$R_6$ is H or $-C(O)R$, R being H or $C_{1-9}$ alkyl,
$R_7$ is H or $C_{1-6}$ alkyl,
$R_8$ is H or $C_{1-6}$ alkyl and n is an integer of 1 to 6.

2. A method of claim 1 wherein $R_5$, $R_7$ and $R_8$ are methyl.

3. A method of claim 1 wherein $R_1$ and $R_2$ are methyl.

4. A method of claim 1 wherein $R_6$ is H.

5. A method of claim 1 wherein $R_6$ is $-C(O)R$.

6. A method of claim 1 wherein n is 2.

7. A method of claim 6 wherein $R_1$, $R_2$, $R_5$, $R_7$ and $R_8$ are methyl.

8. A method of claim 7 wherein $R_6$ is H.

9. A method of claim 7 wherein $R_6$ is $-C(O)R$.

10. A method of claim 1, wherein the compound administered is 3,4-dihydro-2-(2-dimethylaminoethyl)-2,5,7,8-tetra-methyl-2H-1-benzopyran-6-ol or a pharmaceutically acceptable salt thereof.

11. A method of claim 1, wherein the compound administered is 3,4-dihydro-2-(2-dimethylaminoethyl)-2,5,7,8-tetra-methyl-2H-benzopyran-6-yl acetate or a pharmaceutically acceptable salt thereof.

12. A method of claim 1, wherein the compound administered is 3,4-dihydro-2-(2-dimethylaminoethyl)-2,7,8-trimethyl-2H-1-benzopyran-6-ol or a pharmaceutically acceptable salt thereof.

13. A method of claim 1, wherein the compound administered is 3,4-dihydro-2-(2-dimethylaminoethyl)-2,5,8-trimethyl-2H-1-benzopyran-6-ol or a pharmaceutically acceptable salt thereof.

14. A method of claim 1, wherein the compound administered is 3,4-dihydro-2-(2-dimethylaminoethyl)-2,5,7-trimethyl-2H-1-benzopyran-6-ol or a pharmaceutically acceptable salt thereof.

15. A method of claim 1, wherein the compound administered is 3,4-dihydro-2(2-dimethylaminoethyl)-2,5,7,8-tetramethyl-6-(1,1-dimethyl-ethylcarbonyloxy)-2H-1-benzopyran or a pharmaceutically acceptable salt thereof.

16. A method of claim 1, wherein the compound administered is 3,4-dihydro-2-(3-dimethylaminopropyl)-2,5,7,8-tetra-methyl-2H-1-benzopyran-6-ol or a pharmaceutically acceptable salt thereof.

* * * * *